United States Patent
O'Hagan et al.

(10) Patent No.: US 6,534,064 B1
(45) Date of Patent: Mar. 18, 2003

(54) STABILIZED PROTEIN PARTICLES FOR INDUCING CELLULAR IMMUNE RESPONSES

(75) Inventors: Derek O'Hagan, Berkeley, CA (US); Manmohan Singh, Hercules, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/686,345

(22) Filed: Oct. 10, 2000

Related U.S. Application Data

(60) Provisional application No. 60/159,298, filed on Oct. 13, 1999.

(51) Int. Cl.[7] .................. A61K 39/12; A61K 39/29; C07B 63/06; C12Q 1/70; C07C 47/06
(52) U.S. Cl. .................. 424/205.1; 424/199.1; 424/228.1; 424/229.1; 424/208.1; 424/9.34; 424/70.14; 424/70.16; 424/204.1; 424/225.1; 424/207.1; 518/726; 435/8
(58) Field of Search .................. 424/299.1, 205.1, 424/228.1, 229.1, 208.1, 70.14, 70.16, 204.1, 225.1, 207.1; 435/9.34, 8; 518/726

(56) References Cited

U.S. PATENT DOCUMENTS 4,722,840 A * 2/1988 Valenzuela et al. .......... 424/88
5,709,995 A * 1/1998 chisari et al. ............. 424/189.1
6,086,901 A * 7/2000 O'Hagan et al. ........ 424/283.1

FOREIGN PATENT DOCUMENTS

WO    WO 98/50071    11/1998

OTHER PUBLICATIONS

Griffths et al. J. Virol. 1993, vol. 67, No. 6, pp. 3191–3198.*
Ulrich et al. Vaccine 1998, vol. 16, No. 2/3, pp. 272–280.*
Schirmbeck et al. J. Virol. 1994, vol. 68, No. 3, pp. 1418–1425.*
Tindle et al. Virology 1994, vol. 200, pp. 547–557.*
Gilbert et al. Nature Biotechnology, 1997, vol. 15, pp. 1280–1284.*
Wagner et al. Behring Ins. Mitt. 1994, vol. 95, pp. 23–34.*
Tomlinson et al., "Monolithic Albumin Particles as Drug Carriers," *Polymers in Controlled Drug Delivery* Chapter 3; 25–48 (1987).
St. Clair et al., "Crosslinked Protein Crystals for Vaccine Delivery," *Applied Biol. Sciences* 96 (17):9469–9479 (1999).

* cited by examiner

Primary Examiner—James Housel
Assistant Examiner—Bao Qun Li
(74) Attorney, Agent, or Firm—David B. Bonham; Alisa A. Harbin; Robert P. Blackburn

(57) ABSTRACT

A method for producing a cellular immune response in a vertebrate subject comprising administering to the vertebrate subject a vaccine composition comprising a protein particle antigen and a pharmaceutically acceptable excipient is disclosed.

49 Claims, 2 Drawing Sheets

STABILIZED PROTEIN PARTICLES FOR INDUCING CELLULAR IMMUNE RESPONSES

CROSS-REFERENCE TO RELATED APPLICATION

This application is related to provisional patent application Ser. No. 60/159,298, filed Oct. 13, 1999, from which priority is claimed under 35 USC §119(e)(1) and which is incorporated herein by reference in its entirety.

TECHNICAL FIELD

The present invention relates generally to immunogenic agents and to agents which enhance the immune response to a selected antigen. In particular, the invention pertains to the use of protein particles as antigens to elicit cellular immune responses.

BACKGROUND

Numerous vaccine formulations which include attenuated pathogens or subunit protein antigens, have been developed. Conventional vaccine compositions often include immunological adjuvants to enhance cell-mediated and humoral immune responses. For example, depot adjuvants are frequently used which adsorb and/or precipitate administered antigens and which can retain the antigen at the injection site. Typical depot adjuvants include aluminum compounds and water-in-oil emulsions. However, depot adjuvants, although increasing antigenicity, often provoke severe persistent local reactions, such as granulomas, abscesses and scarring, when injected subcutaneously or intramuscularly. Other adjuvants, such as lipopolysacharrides, can elicit pyrogenic responses upon injection and/or Reiter's symptoms (influenza-like symptoms, generalized joint discomfort and sometimes anterior uveitis, arthritis and urethritis). Saponins, such as *Quillaja saponaria,* have also been used as immunological adjuvants in vaccine compositions against a variety of diseases.

More particularly, Complete Freund's adjuvant (CFA) is a powerful immunostimulatory agent that has been successfully used with many antigens on an experimental basis. CFA includes three components: a mineral oil, an emulsifying agent, and killed mycobacteria, such as Mycobacterium tuberculosis. Although effective as an adjuvant, CFA causes severe side effects primarily due to the presence of the mycobacterial component, including pain, abscess formation and fever. CFA, therefore, is not used in human and veterinary vaccines.

Incomplete Freund's adjuvant (IFA) is similar to CFA but does not include the bacterial component. IFA, while not approved for use in the United States, has been used elsewhere in human vaccines for influenza and polio and in veterinary vaccines for rabies, canine distemper and foot-and-mouth disease. However, evidence indicates that both the oil and emulsifier used in IFA can cause tumors in mice.

Despite the presence of such adjuvants, conventional vaccines often fail to provide adequate protection against the targeted pathogen. In this regard, there is growing evidence that vaccination against intracellular pathogens, such as a number of viruses, should target both the cellular and humoral arms of the immune system. More particularly, cytotoxic T-lymphocytes (CTLs) play an important role in cell-mediated immune defense against intracellular pathogens such as viruses and tumor-specific antigens produced by malignant cells. CTLs mediate cytotoxicity of virally infected cells by recognizing viral determinants in conjunction with class I MHC molecules displayed by the infected cells. Cytoplasmic expression of proteins is a prerequisite for class I MHC processing and presentation of antigenic peptides to CTLs. However, immunization with killed or attenuated viruses often fails to produce the CTLs necessary to curb intracellular infection. Furthermore, conventional vaccination techniques against viruses displaying marked genetic heterogeneity and/or rapid mutation rates that facilitate selection of immune escape variants, such as HIV or influenza, are problematic. Accordingly, alternative techniques for vaccination have been developed.

Particulate carriers with adsorbed or entrapped antigens have been used in an attempt to circumvent these problems and in attempts to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as polymer particles derived from poly (lactides) and poly(lactide-co-glycolides), known as PLG. While offering significant advantages over other more toxic systems, antigen-containing PLG particles suffer from some drawbacks. For example, large scale production and manufacturing of particulate carriers may be problematic due to the high cost of the polymers used in the manufacture the particulate carriers.

Liposomes have also been employed in an effort to overcome these problems. Liposomes are microscopic vesicles formed from lipid constituents such as phospholipids which are used to entrap pharmaceutical agents. Although the use of liposomes as a drug delivery system alleviates some of the problems described above, liposomes exhibit poor stability during storage and use, and large scale production and manufacturing of liposomes is problematic.

International Publication No. WO 98/50071 describes the use of viral-like particles (VLPs) as adjuvants to enhance immune responses of antigens administered with the VLPs. St. Clair et al. describe the use of protein crystals to enhance humoral and cellular responses. (St. Clair, N. et al, *Applied Biol. Sci.,* 96:9469–9474, 1999).

Despite the above described adjuvant and antigen-presentation systems, there is a continued need for effective, safe and cost-efficient vaccines with improved purity, stability and immunogenicity.

SUMMARY OF THE INVENTION

The inventors herein have found, surprisingly, that protein particles are self-sustaining immunogenic agents which produce cellular immune responses. In particular, the active ingredient is also the delivery system, i.e., the protein particles serve as the antigen and the delivery system. Additionally, the inventors have discovered that the protein particles have several advantages (i) the ease of manufacture, (ii) they are more cost-effective to manufacture than existing agents, (iii) they provide for superior immune responses, and (iv) they have reduced toxicity and eliminate the undesirable side-effects observed with other vaccine formulations. Accordingly, then, the invention is primarily directed to the use of such protein particles as antigens.

In one embodiment, the invention is directed to an immunogenic composition comprising selected first antigen and a pharmaceutically acceptable excipient, wherein the selected first antigen is a protein particle, and further wherein the protein particle antigen is capable of producing a cellular immune response. In preferred embodiments, the protein particle is formed from a protein selected from the group consisting of a viral, a fungal, a bacteria, an avian or a mammalian protein. In more preferred embodiments, the protein is herpes simplex virus type 2 glycoprotein B (HSV gB2), hepatitis C virus (HCV) or a human immunodeficiency virus (HIV) protein.

In another embodiment, the immunogenic composition further comprising an adjuvant, wherein the adjuvant is encapsulated within, adsorbed or conjugated on to, or mixed with the protein particle.

In an additional embodiment, the immunogenic composition further comprises a second antigen, wherein the second antigen is distinct from the first antigen, i.e. the protein particle. The second antigen may be a soluble or neutralizing antigen, it may be conjugated on to the protein particle, or it may be associated with a carrier (for example, the second antigen may be encapsulated within, adsorbed or conjugated on to, or mixed with the carrier). In certain preferred embodiments, the carriers include, but are not limited to proteins, polysaccharides, polylactic acids, polyglycollic acids, polymeric amino acids, amino acid copolymers, lipid aggregates (such as oil droplets or liposomes), polymeric particulate carriers, and inactive virus particles. In more preferred embodiments, the carriers comprise a poylmeric particle, wherein the polymeric particle comprises a polymer selected from the group consisting of a poly($\alpha$-hydroxy acid), a polyhydroxy butyric acid, a polycaprolactone, a polyorthoester, and a polyanhydride.

In an alternative embodiment, the invention is directed to an immunogenic composition comprising a selected first antigen and a pharmaceutically acceptable excipient, wherein the selected first antigen is a protein particle, and further wherein the protein particle is produced by a process comprising the steps of:

(a) providing an aqueous solution of a protein;

(b) adding a precipitation agent to the aqueous solution of the protein and stirring the resulting mixture to form the protein particle;

(c) stabilizing said protein particle by a stabilizing treatment; and (d) recovering the protein particles from the aqueous solution.

In an alternative embodiment, the aqueous solution is step (a) further comprises an acid, wherein the acid is acetic acid, glycolic acid, hydroxybutyric acid, hydrochloric acid or lactic acid. In preferred embodiments, the precipitation agent comprises oils, hydrocarbons or coacervation agents. In additional preferred embodiments, the stabilizing treatment comprises heat treatment or by treatment with a chemical cross-linking agent.

In preferred embodiments, the protein particle is capable of producing a cellular immune response; and is formed from a protein selected from the group consisting of a viral, a fungal, a bacterial, an avian or a mammalian protein. In more preferred embodiments, the protein is herpes simplex virus type 2 glycoprotein B (HSV gB2), hepatitis C virus (HCV) or a human immunodeficiency virus (HIV) protein. In certain preferred embodiments, the cellular immune response can be a cytotoxic-T lymphocyte (CTL) response. In another embodiment, the immunogenic or vaccine composition further comprises an adjuvant and/or a second antigen as described above, wherein the protein particle is capable of functioning as an antigen and/or an adjuvant.

In another embodiment, the subject invention is directed to a method for producing a cytotoxic-T lymphocyte (CTL) response in a vertebrate subject comprising administering to the vertebrate subject an immunogenic or vaccine composition comprising the protein particle as described above. The protein particle is administered in an amount effective for eliciting a cytotoxic-T lymphocyte (CTL) response in the vertebrate subject. The protein particles can be co-administered to the subject prior or subsequent to, or concurrent with, an adjuvant and/or a second antigen.

In another embodiment, the invention is directed to a method of immunization which comprises administering to a vertebrate subject a therapeutically effective amount of the immunogenic or vaccine composition comprising the protein particle as discussed above.

These and other embodiments of the present invention will readily occur to those of ordinary skill in the art in view of the disclosure herein.

DETAILED DESCRIPTION OF THE INVENTION

Figure 1:
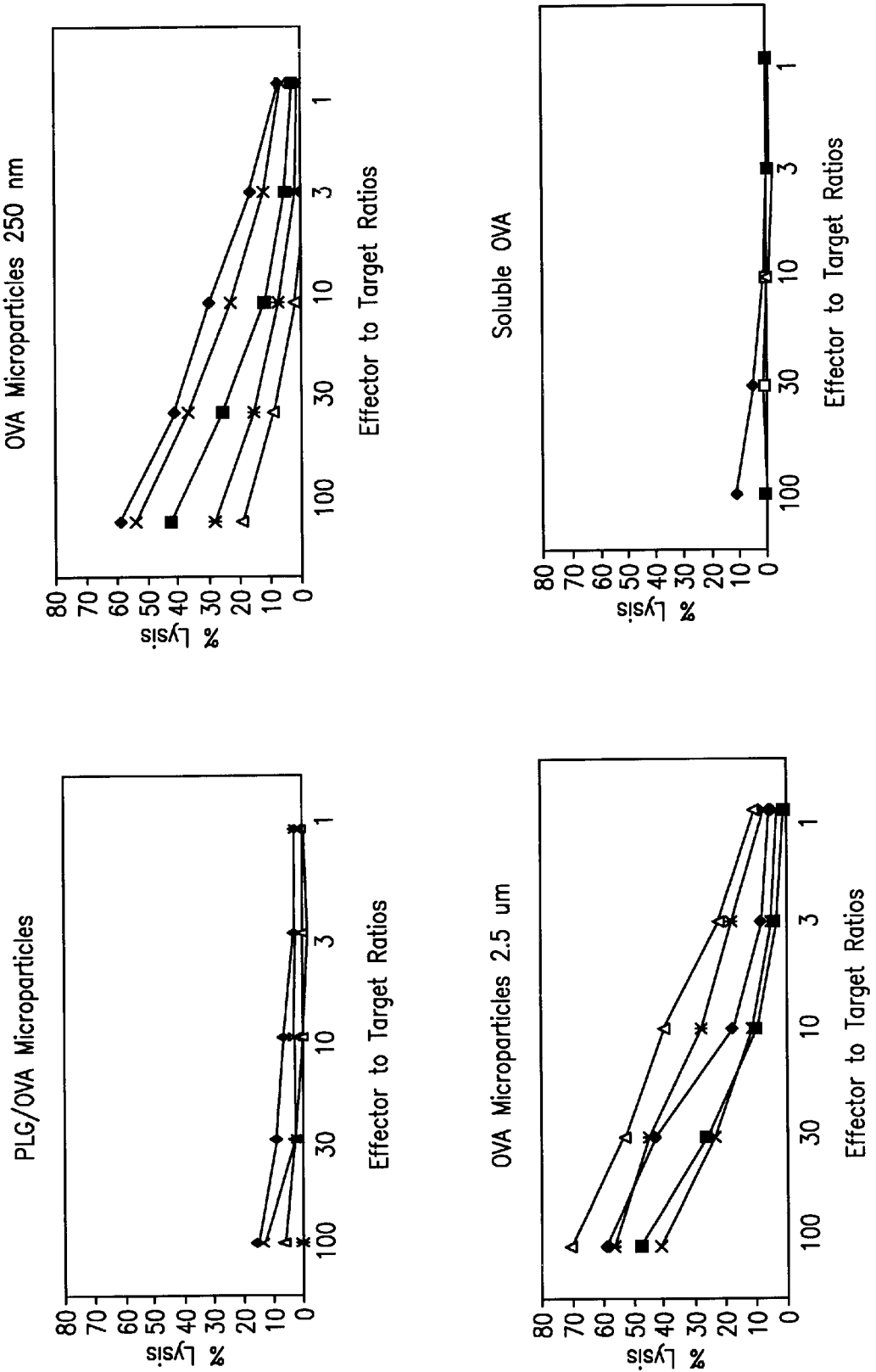
FIG. 1 illustrates the effect of ovalbumin (OVA), OVA-protein particles, and PLG/OVA-entrapped particles on percent specific lysis of targets.

The practice of the present invention will employ, unless otherwise indicated, conventional methods of virology, chemistry, biochemistry, recombinant technology, immunology and pharmacology, within the skill of the art. Such techniques are explained fully in the literature. See, e.g., *Virology*, 3rd Edition, vol. I & II (B. N. Fields and D. M. Knipe, eds., 1996); *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); *Handbook of Experimental Immunology*, Vols. I–IV (D. M. Weir and C. C. Blackwell, eds., 1986, Blackwell Scientific Publications); Sambrook et al., *Molecular Cloning: A Laboratory Manual* (2nd Edition, 1989); and *DNA Cloning: A Practical Approach*, vol. I & II (D. Glover, ed.).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

As used herein, the term "protein particle" refers to a particle made from a protein, wherein the term "protein" refers to peptides, polypeptides, metalloproteins, glycoproteins and lipoproteins. In preferred embodiments, proteins from which the protein particles are formed include, without limitation, viral proteins, fungal proteins, bacterial proteins, avian proteins, mammalian proteins and eucaryotic proteins, such as but not limited to albumin, gelatin, zein, casein, collagen and fibrinogen. In more preferred embodiments, proteins from which the protein particles are formed include, without limitation, proteins from the herpes virus family, including proteins derived from herpes simplex virus (HSV) types 1 and 2, such as HSV-1 and HSV-2 glycoproteins gB, gD and gH; proteins derived from cytomegalovirus (CMV) including CMV gB and gH; proteins derived from hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV); proteins, including gp120, gp160, gp41, p24gag and p55gag envelope proteins, derived from HIV such as, including members of the various genetic subtypes of HIV isolates $HIV_{IIIb}$, $HIV_{SF2}$, $HIV_{LAV}$, $HIV_{LAI}$, $HIV_{MN}$, $HIV-1_{CM235}$, $HIV-1_{US4}$, HIV-2; proteins derived from simian immunodeficiency virus (SIV); proteins derived from Neisseria meningitidis (A, B, C, Y), Hemophilus influenza type B (HIB), *Helicobacter pylori;* human serum albumin and ovalbumin. Methods for producing particular protein particles are known in the art and discussed more fully below.

The protein particles have the following physical characteristics. The protein particles are approximately about 150 nm to about 10 µm, preferably about 200 nm to about 4 µm, more preferably about 250 nm to about 3 µm. The protein particles are generally spherical in shape and possess a diameter of about 200 nm to about 10 µm, preferably of about 500 nm to about 5 µm, more preferably of about 1 µm to about 3 µm. Generally, the protein particles are obtained by denaturing and cross-linking the protein, followed by stabilization of the cross-linked protein. Methods for producing particular protein particles are discussed more fully below.

Several detection techniques may be used in order to confirm that proteins have taken on the conformation of protein particles. Such techniques include electron microscopy, X-ray crystallography, and the like. See, e.g., Baker et al., *Biophys. J.* (1991) 60:1445–1456; Hagensee et al., *J. Virol.* (1994) 68:4503–4505. For example, cryoelectron microscopy can be performed on vitrified aqueous samples of the protein particle preparation in question, and images recorded under appropriate exposure conditions.

The terms "polypeptide" and "protein" refer to polymers of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to the native sequence, so long as the protein is capable of acting as an antigen and eliciting a CTL response.

Preferred substitutions are those which are conservative in nature, i.e., those substitutions that take place within a family of amino acids that are related in their side chains. Specifically, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide.

A protein particle (i.e. a selected first antigen) is "distinct from" a selected second antigen when the second antigen is not entrapped within the protein particles and/or the second antigen and protein particles are not expressed together as a fusion protein. However, a protein particle is considered "distinct from" a selected second antigen even if there is a loose physical association between the second antigen and protein particles so long as the second antigen is not covalently bound to, entrapped within or adsorbed to the surface of the protein particle.

An "antigen" refers to a molecule containing one or more epitopes (either linear, conformational or both) that elicit an immunological response, as defined below. The term is used interchangeably with the term "immunogen." Normally, a B-cell epitope will include at least about 5 amino acids but can be as small as 3–4 amino acids. A T-cell epitope, such as a CTL epitope, will include at least about 7–9 amino acids, and a helper T-cell epitope at least about 12–20 amino acids. The term "antigen" denotes both subunit antigens, i.e., antigens which are separate and discrete from a whole organism with which the antigen is associated in nature, as well as killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

For purposes of the present invention, antigens can be derived from any of several known viruses, bacteria, parasites and fungi, as described more fully below. The term also intends any of the various tumor antigens. Furthermore, for purposes of the present invention, an "antigen" refers to a polynucleotide and a protein which includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

By "an *H. pylori* lysate" is meant an extract or lysate derived from an *H. pylori* Type I or Type II whole bacterium which includes one or more *H. pylori* antigens. Thus, the term denotes crude extracts that contain several *H. pylori* antigens, as well as relatively purified compositions derived from such crude lysates which include only one or few such antigens. Such lysates are prepared using techniques well known in the art.

Representative antigens that may be present in such lysates, either alone or in combination, include one or more antigens derived from the *H. pylori* adhesins such as, but not limited to, a 20 kDa α-acetyl-neuraminillactose-binding fibrillar haemagglutinin (HpaA), a 63 kDa protein that binds phosphatidyl-ethanolamine and gangliotetraosyl ceramide, and a conserved fimbrial pilus-like structure. See, e.g., Telford et al., *Trends in Biotech.* (1994) 12:420–426 for a description of these antigens. Other antigens that may be present in the lysate include epitopes derived from any of the various flagellins such as the major flagellin, FlaA and the minor flagellin, FlaB. In this regard, the flagella of *H. pylori* are composed of FlaA and FlaB, each with a molecular weight of approximately 53 kDa. Another representative antigen includes *H. pylori* urease which is associated with the outer membrane and the periplasmic space of the bacterium. The holoenzyme is a large complex made up of two subunits of 26.5 kDa (UreA) and 61 kDa (UreB), respectively. Epitopes derived from the holoenzyme, either of the subunits, or a combination of the three, can be present and are captured under the definition of "urease" herein. Another representative antigen that may be present in the lysate or used in further purified form includes the an *H. pylori* heat shock protein known as "hsp60." The DNA and corresponding amino acid sequences for hsp60 are known. See, e.g., International Publication No. WO 93/18150, published Sep. 16, 1993. The full-length hsp60 antigen shown has about 546 amino acids and a molecular weight of about 58 kDa. The VacA and CagA antigens may also be present in such lysates. It is to be understood that the lysate can also include other antigens not specifically described herein.

By "VacA antigen" is meant an antigen as defined above which is derived from the antigen known as the *H. pylori* Type I Cytotoxin. The VacA protein induces vacuolization in epithelial cells in tissue culture and causes extensive tissue damage and ulceration when administered orally to mice. The DNA and corresponding amino acid sequences for VacA are known and reported in, e.g., International Publication No. WO 93/18150, published Sep. 16, 1993. The gene for the VacA antigen encodes a precursor of about 140 kDa that is processed to an active molecule of about 90–100 kDa. This molecule, in turn, is slowly proteolytically cleaved to generate two fragments that copurify with the intact 90 kDa molecule. See, Telford et al., *Trends in Biotech.* (1994) 12:420–426. Thus, the definition of "VacA antigen" as used herein includes the precursor protein, as well as the processed active molecule, proteolytic fragments thereof or portions or muteins thereof, which retain specific reactivity with antibodies present in a biological sample from an individual with *H. pylori* Type I infection.

By "CagA antigen" is meant an antigen as defined above which is derived from the *H. pylori* Type I cytotoxin associated immunodominant antigen. CagA is expressed on the bacterial surface. The DNA and corresponding amino acid sequences for CagA are known. See, e.g., International Publication No. WO 93/18150, published Sep. 16, 1993. The full-length CagA antigen described therein includes about 1147 amino acids with a predicted molecular weight of about 128 kDa. The native protein shows interstrain size variability due to the presence of a variable number of repeats of a 102 bp DNA segment that encodes repeats of a proline-rich amino acid sequence. See, Covacci et al., *Proc. Natl. Acad. Sci. USA* (1993) 90:5791–5795. Accordingly, the reported molecular weight of CagA ranges from about 120–135 kDa. Hence, the definition of "CagA antigen" as used herein includes any of the various CagA variants, fragments thereof and muteins thereof, which retain the ability to react with antibodies in a biological sample from an individual with *H. pylori* Type I infection. For example, the CagA polypeptide depicted in FIG. 3 is a truncated protein of 268 amino acids and includes Glu-748 to Glu-1015, inclusive, of the full-length molecule. Further, the definition of "CagA antigen" as used herein includes Nap protein of *H. pylori* antigen. See, e.g. PCT IB99/00695 for a description of nap protein of *H. pylori* and methods to purify the same.

A "purified" protein or polypeptide is a protein which is recombinantly or synthetically produced, or isolated from its natural host, such that the amount of protein present in a composition is substantially higher than that present in a crude preparation. In general, a purified protein will be at least about 50% homogeneous and more preferably at least about 80% to 90% homogeneous.

An "immunological response" to an antigen or composition is the development in a subject of a humoral and/or a cellular immune response to the antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

An immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by, e.g., but not limited to B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An immunogenic or vaccine composition which contains a protein particle antigen of the present invention, or an immunogenic or vaccine composition comprising an adjuvant and/or a second antigen which is coadministered with the subject protein particle antigen, displays "enhanced immunogenicity" when it possesses a greater capacity to elicit an immune response than the immune response elicited by an equivalent amount of the antigen administered using a different delivery system, e.g., wherein the antigen is administered as a soluble protein, or as an antigen-containing particulate carrier (e.g., the antigen is adsorbed on to or encapsulated within a PLG particle). Thus, an immunogenic or vaccine composition may display "enhanced immunogenicity" because the antigen is more strongly immunogenic or because a lower dose or fewer doses of antigen are necessary to achieve an immune response in the subject to which the antigen is administered. Such enhanced immunogenicity can be determined by administering the protein particle composition and antigen controls to animals and comparing antibody titers and/or cellular-mediated immunity against the two using standard assays described above.

For purposes of the present invention, an "effective amount" of a protein particle antigen will be that amount which elicits an immunological response when administered, or enhances an immunological response to a coadministered antigen.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual along with the protein particle formulation without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

B. General Methods

Central to the present invention is the surprising discovery that protein particles can serve as antigens to enhance humoral and/or cell-mediated immune responses in a vertebrate subject when the protein particles are administered. The protein particle is self-sustaining, i.e., the protein particle is the antigen as well as the delivery system for the active ingredient. Thus, the present invention does not require the use of carriers, such as polymers including PLG and the like, since the antigen of interest, in the form of a protein particle, need not be adsorbed on to, or entrapped within a carrier particle in order to elicit a cellular immune response. Additionally, antigen size is not limited since the system does not depend on encapsulation of the antigen. Accordingly, the present system is useful with a wide variety of antigens and provides a powerful tool to prevent and/or treat a large number of infections.

Protein particles for use as antigens can be formed from almost any protein, or combination of proteins or fragments thereof, that have the capability of forming particles under appropriate conditions. In particular, the protein particles of the present invention may be formed either by chemical precipitation of a purified protein, by using chemical cross-linking agents, or by heat stabilization, as described in detail below. Additionally, the protein particles of the invention are structurally different from VLPs. The protein particles have the following physical characteristics. The protein particles are approximately about 150 nm to about 10 $\mu$m, preferably about 200 nm to about 4 $\mu$m, more preferably about 250 nm to about 3 $\mu$m. The protein particles are generally spherical in shape and possess a diameter of about 200 nm to about 10 $\mu$m, preferably of about 500 nm to about 5 $\mu$m, more preferably of about 1 $\mu$m to about 3 $\mu$m.

In contrast, virus-like particles (VLPs) can form spontaneously upon recombinant expression of the protein in an appropriate expression system. Generally, the VLPs are formed within a homogenous matrix, such as a membrane, and can be secreted from the expression system. Further, VLPs are approximately about 50 nm, and are spherical in shape and possess a diameter of about 40 nm to about 100 nm. However, very few proteins spontaneously form VLPs.

A particular advantage of the present invention is the ability of the protein particles to enhance immunogenicity, such as by generating cell-mediated immune responses in a vertebrate subject. The ability of the protein particles of the present invention to elicit a cell-mediated immune response provides a powerful tool against infection by a wide variety of pathogens. Accordingly, the protein particles of the present invention can be incorporated into vaccine compositions.

An additional advantage of the present invention is the discovery that the protein particles are more cost-effective to manufacture, provide for superior immune responses and have reduced toxicity and other undesirable side-effects as compared to polymeric particles, such as PLG-microparticles. Accordingly, the present system is useful with a wide variety of antigens and provides a powerful tool to prevent and/or treat a large number of infections.

Protein particles for use as antigens can be formed from proteins, such as peptides, polypeptides, metalloproteins, glycoproteins and lipoproteins. In preferred embodiments, proteins from which the protein particles are formed include, without limitation, viral proteins, fungal proteins, bacterial proteins, avian proteins, mammalian proteins and eucaryotic proteins. In more preferred embodiments, proteins from which the protein particles are formed include, without limitation, proteins from the herpes virus family, including proteins derived from herpes simplex virus (HSV) types 1 and 2, such as HSV-1 and HSV-2 glycoproteins gB, gD and gH; proteins derived from cytomegalovirus (CMV) including CMV gB and gH; proteins derived from hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV); proteins, including gp120, gp160, gp41, p24gag and p55gag envelope proteins, derived from HIV such as, including members of the various genetic subtypes of HIV isolates $HIV_{IIIb}$, $HIV_{SF2}$, $HIV_{LAV}$, $HIV_{LA1}$, $HIV_{MN}$, $HIV-1_{CM235}$, $HIV-1_{US4}$, HIV-2; proteins derived from simian immunodeficiency virus (SIV); proteins derived from Neisseria meningitidis (A, B, C, Y), Hemophilus influenza type B (HIB), *Helicobacter pylori;* human serum albumin and ovalbumin, as discussed more fully below. In an alternative embodiment, the protein particles can be formed from a combination of one or more proteins, or the combination of a protein and a second antigen, wherein the second antigen is distinct from the protein.

Antigens, therefore, can be derived from a wide variety of viruses, bacteria, fungi, plants, protozoans and other parasites. For example, the present invention will find use for stimulating an immune response against a wide variety of proteins from the herpes virus family, including proteins derived from herpes simplex virus (HSV) types 1 and 2, such as HSV-1 and HSV-2 gB, gD, gH, VP16 and VP22; antigens derived from varicella zoster virus (VZV), Epstein-Barr virus (EBV) and cytomegalovirus (CMV) including CMV gB and gH; and antigens derived from other human herpes viruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

Additionally, immune responses to antigens from the hepatitis family of viruses, including hepatitis A virus (HAV), hepatitis B virus (HBV), hepatitis C virus (HCV), the delta hepatitis virus (HDV), hepatitis E virus (HEV), and hepatitis G virus, can also be conveniently enhanced using the protein particles. By way of example, the HCV genome encodes several viral proteins, including E1 (also known as E) and E2 (also known as E2/NSI), NS3, NS4, NS5, and the like, which will find use with the present invention (see, Houghton et al. *Hepatology* (1991) 14:381–388, for a discussion of HCV proteins, including E1 and E2). The δ-antigen from HDV can also be used with the present protein particle system (see, e.g., U.S. Pat. No. 5,389,528, for a description of the δ-antigen).

Similarly, influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759–767; Webster et al. "Antigenic variation among type A influenza viruses," p. 127–168. In: P. Palese and D. W. Kingsbury (ed.), *Genetics of influenza viruses.* Springer-Verlag, N.Y.). Thus, these antigens may elicit an immune response when administered as protein particles. Alternatively, the immune response to any of these antigens may be enhanced when they are coadministered with the subject protein particle antigens.

Other antigens of particular interest to be used in the subject protein particle compositions include antigens and polypeptides derived therefrom from human papillomavirus (HPV), such as one or more of the various early proteins including E6 and E7, tick-borne encephalitis viruses, HIV-1 (also known as HTLV-III, LAV, ARV, hTLR, etc.), including but not limited to antigens from the isolates $HIV_{IIIb}$, $HIV_{SF2}$, $HIV_{LAV}$, $HIV_{LAI}$, $HIV_{MN}$) such as gp120, gp41, gp160, gag and pol (see, e.g., Myers et al. Los Alamos Database, Los Alamos National Laboratory, Los Alamos, N. Mex. (1992); Myers et al., *Human Retroviruses and Aids,* 1990, Los Alamos, N. Mex.: Los Alamos National Laboratory; and Modrow et al., *J. Virol.* (1987) 61:570–578, for a comparison of the envelope gene sequences of a variety of HIV isolates).

Particularly preferred viral antigens are derived from other viruses such as without limitation, proteins from members of the families Picomaviridae (e.g., polio viruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae, e.g., HTLV-I; HTLV-II; HIV-1; HIV-2; simian immundeficiency virus (SIV) among others. See, e.g. Virology, 3rd Edition (W. K. Joklik ed. 1988); *Fundamental Virology,* 2nd Edition (B. N. Fields and D. M. Knipe, eds. 1991), for a description of these and other viruses.

Particularly preferred bacterial antigens are derived from organisms that cause diphtheria, tetanus, pertussis, meningitis, and other pathogenic states, including, without limitation, antigens derived from Corynebacterium diphtheriae, *Clostridium tetani,* Bordetella pertusis, Neisseria meningitidis, including serotypes Meningococcus A, B, C, Y and WI35 (MenA, B, C, Y and WI35), Haemophilus influenza type B (Hib), and *Helicobacter pylori.* Examples of parasitic antigens include those derived from organisms causing malaria and Lyme disease.

In more preferred embodiments, the bacterial antigens are derived from *H. pylori. H. pylori* bacteria are divided into two groups, Type I and Type II, based on the presence or absence of specific proteins. For example, both Type I and Type II bacteria produce ureases and a number of adhesins. On the other hand, only *H. pylori* Type I strains produce VacA and CagA. (International Publication No. WO 93/18150, published Sep. 16, 1993). Accordingly, the compositions of the present invention may include one or more of VacA, CagA, *H. pylori* urease, an *H. pylori* lysate as described above, *H. pylori* heat shock protein hsp60, and the like. For example, a broad-based vaccine may contain antigens specific to *H. pylori* Type I, such as VacA and CagA, as well as antigens common to *H. pylori* Types I and II, such as urease. (For a further discussion of *H. pylori* antigens for use herein, see International Publication Nos. WO 93/18150, published Sep. 16, 1993 and WO 98/27432, published Jun. 25, 1998).

In alternative embodiments, preferred bacterial antigens are derived from Neisseria meningitidis. Meningococci are divided into serological groups based on the immunological characteristics of capsular and cell wall antigens. Currently recognized serogroups include A, B, C, D, W-135, X, Y, Z and 29E. Capsular polysaccharide-based vaccines have been developed against meningococcal disease caused by serogroups A (MenA), B (MenB), C (Men C), Y (Men Y) and W135 (Men W135). (For a further discussion of MenB antigens for use herein, see International Publication Nos. WO 98/08543, published Mar. 5, 1998; WO 98/08874, published Mar. 5, 1998, WO 99/10372, published Mar. 4, 1999; US99/09346, IB98/01665, and IB99/00103).

Combinations of antigens derived from the organisms above can be conveniently used to elicit immunity to multiple pathogens in a single vaccine. For example, a particularly preferred combination is a combination of bacterial surface oligosaccharides derived from MenC and Hib, conjugated to a nontoxic mutant carrier derived from a bacterial toxin, such as a nontoxic mutant of diphtheria toxin known as $CRM_{197}$. This conjugate is useful for preventing bacterial meningitis and is described in International Publication No. WO 96/14086, published May 17, 1996.

Furthermore, the methods described herein provide means for treating a variety of malignant cancers. For example, the system of the present invention can be used to enhance both humoral and cell-mediated immune responses to particular proteins specific to a cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993):82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used to mount an immune response to a wide variety of antigens and hence to treat or prevent a large number of diseases.

Methods and suitable conditions for forming particles from a wide variety of proteins are known in the art. For example, in the suspension cross-linking process, a solution of a protein is added to an immiscible liquid or an oil phase. The protein is dissolved in an appropriate solvent, such as an alcohol (methanol, ethanol, isopropanol, and the like), a ketone (methyl ethyl ketone, acetone, and the like), a glycol (ethylene glycol, propylene glycol, and the like) or an amide solvent (e.g., acetamide), containing between 5% to about 90% of water. A precipitation agent is added to the protein solution form a protein particle. Oils such as mineral oil, silicone oil, or vegetable oil; hydrocarbons, such as hexane, heptane, dodecane, and high boiling petroleum ether; and coacervation agents such as acetone, ethanol, ispropanol, and the like, are useful as precipitation agents. The protein particles are dispersed by high speed stirring, and stabilized using stabilization treatment, such as heat treatment or by treatment with a chemical cross-linking agent. In particular, stabilization is achieved by heating of the suspension to a temperature about 30° C. to about 150° C., preferably of about 35° C. to about 120° C., more preferably of about 40° C. to about 100° C. Alternatively the protein particles are stabilized by treatment with a chemical cross-linking agent, such as gluteraldehyde, butadione, and the like. See, e.g. WO 96/10992; *Polymers in Controlled Drug Delivery,* Eds. Illum, L. and Davis, S. S. (Wright, 1987) Chapter 3, pg 25; Torrado, J. J. et al., *International Journal of Pharmaceutics,* (1989) 51:85–93; Chen, G. Q et al., *Journal of Microencapsulation,* (1994) 11(4):395–407.

In particular, an aqueous solution of a protein, preferably about 0.1 to about 20% protein solution, more preferably about 0.5 to about 10%, and even more preferably about 1 to about 5% protein solution, is treated with an acid, until the pH is about 1 to about 6, preferably about 1.5 to about 5, more preferably about 2 to about 4, wherein the acid includes, but is not limited to, acetic acid, glycolic acid, hydroxybutyric acid, hydrochloric acid, lactic acid, and the like. The solution is stirred at high speed, preferably at about 1,000 to about 25,000 rpm, more preferably about 2,000 to about 15,000, even more preferably about 5,000 to about 10,000 rpm for about 1 minute to about 60 minutes, preferably about 5 to about 45 minutes, more preferably about 10 to about 30 minutes. A coacervation agent is added to the stirring solution to form the protein particles, and the mixture is stirred for about 1 minute to about 60 minutes, preferably about 5 to about 45 minutes, more preferably about 10 to about 30 minutes. Coacervation agents include, but are not limited to acetone, ethanol, ispropanol, and the like. The coacervation agent is optionally evaporated and the protein particles are stabilized by heating the mixture at about 30 to about 70° C., preferably at about 35 to about 65° C., more preferably about 40 to about 60° C., for about 1 minute to about 60 minutes, preferably about 5 to about 45 minutes, more preferably about 10 to about 30 minutes, with stirring at about 1,000 to about 25,000 rpm, more preferably about 2,000 to about 15,000, even more preferably about 5,000 to about 10,000 rpm. The protein particles are sized, for example in a Malvern Master sizer.

In an alternative process, an aqueous solution of the protein, as described above, is added to a precipitation agent, such as mineral oil, silicone oil, or vegetable oil, and/or hydrocarbons, such as hexane, heptane, dodecane, and high boiling petroleum ether. The emulsion is stirred at high speed, preferably at about 1,000 to about 25,000 rpm, more preferably about 2,000 to about 15,000, even more preferably about 5,000 to about 10,000 rpm for about 1 minute to about 60 minutes, preferably about 5 to about 45 minutes, more preferably about 10 to about 30 minutes. The mixture is heated at about 30 to about 70° C., preferably at about 35 to about 65° C., more preferably about 40 to about 60° C., for about 1 minute to about 60 minutes, preferably about 5 to about 45 minutes, more preferably about 10 to about 30 minutes, with stirring at about 1,000 to about 25,000 rpm, more preferably about 2,000 to about 15,000, even more preferably about 5,000 to about 10,000 rpm to stabilize the protein particles. The mixture is centrifuged and the protein particles are collected. The protein particles are sized, for example in a Malvern Master sizer.

Once obtained, the protein particle of the present invention can be incorporated into immunogenic or vaccine compositions optionally comprising an adjuvant and/or a selected second antigen. The adjuvant and/or the second antigen can be administered separately, either simultaneously with, just prior to, or subsequent to, the administration of the protein particle composition. The vaccine compositions can be used both for treatment and/or prevention of infection. Furthermore, the formulations of the invention comprising the protein particles may be used to enhance the activity of selected second antigens produced in vivo, i.e., in conjunction with DNA immunization.

The protein particle antigens can be used in compositions for immunizing a vertebrate subject against one or more selected pathogens or against subunit antigens derived therefrom, or for priming an immune response to one or several antigens. Antigens that can be administered as a second antigen with the protein particle antigens include proteins, polypeptides, antigenic protein fragments, oligosaccharides, polysaccharides, and the like. Similarly, an oligonucleotide or polynucleotide, encoding a desired antigen, can be administered with the protein particle antigens for in vivo expression.

As explained above, the protein particle formulations may or may not contain a second antigen of interest. For example, the protein particles may be formed from a combination of an appropriate protein and an antigen, or the antigens can be administered separately from the protein particle compositions at the same or at different sites. In any event, one or more selected antigens will be administered in a "therapeutically effective amount" such that an immune response can be generated in the individual to which it is administered. The exact amount necessary will vary depending on the subject being treated; the age and general condition of the subject to be treated; the capacity of the subject's immune system to synthesize antibodies and/or mount a cell-mediated immune response; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. In general, a "therapeutically effective" amount of antigen will be an amount on the order of about 0.1 μg to about 1000 μg, more preferably about 1 μg to about 100 μg.

Similarly, the protein particle antigens will be present in an amount such that the second antigen displays "enhanced immunogenicity," as defined above. Amounts which are effective for eliciting an enhanced immune response can be readily determined by one of skill in the art.

The compositions may additionally contain one or more "pharmaceutically acceptable excipients or vehicles" such as water, saline, glycerol, ethanol, etc. Additionally, auxiliary substances, such as wetting or emulsifying agents, biological buffers, and the like, may be present in such vehicles. A biological buffer can be virtually any solution which is pharmacologically acceptable and which provides the adjuvant formulation with the desired pH, i.e., a pH in the physiological range. Examples of buffer solutions include saline, phosphate buffered saline, Tris buffered saline, Hank's buffered saline, growth media such as Eagle's Minimum Essential Medium ("MEM"), and the like.

The second antigen is optionally associated with a carrier (e.g., the antigen may be encapsulated within, or adsorbed on to the carrier), wherein the carrier is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), polymeric particulate carriers, inactive virus particles and the like. Additionally, these carriers may function as additional immunostimulating agents. Furthermore, the antigen may be conjugated to a bacterial toxoid, such as toxoid from diphtheria, tetanus, cholera, etc. Examples of polymeric particulate carriers include particulate carriers formed from materials that are sterilizable, non-toxic and biodegradable. Such materials include, without limitation, poly(α-hydroxy acid), polyhydroxybutyric acid, polycaprolactone, polyorthoester and polyanhydride. Preferably, microparticles for use with the present invention are derived from a poly(a-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered second antigen. (for a further discussion of particulate carriers for use herein, see commonly owned, U.S. patent application Ser. No. 09/124,533, filed on Jul. 29, 1998).

The adjuvant/second antigen may be conjugated on to the surface of the protein particle any of the several methods known in the art ( see, e.g., *Bioconjugate Techniques,* Greg. T. Hermanson Ed., Academic Press, New York. 1996). For example, protein-protein (i.e. protein particle-second antigen) conjugation could be carried by using sulfo-SMCC linkers (sulfosuccinimidyl esters) for conjugation using standard protocols.

Adjuvants may also be used to enhance the effectiveness of the pharmaceutical compositions. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see International Publication No. WO 99/30739, published Jun. 24, 1999); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), adjuvants derived from the CpG family of molecules, CpG dinucleotides and synthetic oligonucleotides which comprise CpG motifs (see, e.g., Krieg et al., *Nature,* 374:546 (1995) and Davis et al., *J. Immunol.,* 160:870–876 (1998)) and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipahitoyl-sn-glycero-3-huydroxyphosphoryloxy)-ethylamine (MTP-PE), etc.

Once formulated, the compositions of the invention can be administered parenterally, e.g., by injection. The compositions can be injected either subcutaneously, intraperitoneally, intravenously or intramuscularly. Other modes of administration include oral and pulmonary administration, suppositories, mucosal and transdermal applications. Dosage treatment may be a single dose schedule or a multiple dose schedule. A multiple dose schedule is one in which a primary course of vaccination may be with 1–10 separate doses, followed by other doses given at subsequent time intervals, chosen to maintain and/or reinforce the immune response, for example at 1–4 months for a second dose, and if needed, a subsequent dose(s) after several months. The dosage regimen will also, at least in part, be determined by the need of the subject and be dependent on the judgment of the practitioner. Furthermore, if prevention of disease is desired, the vaccines are generally administered prior to primary infection with the pathogen of interest. If treatment is desired, e.g., the reduction of symptoms or recurrences, the vaccines are generally administered subsequent to primary infection.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of Small Ovalbumin (OVA) Protein Particles

Ovalbumin (OVA, 200 mg) was dissolved in distilled water (10 ml) to form a 2% protein solution. Lactic acid (100 μl) was added to the OVA-solution until the pH was reduced to about 4.5–5.0. The solution was stirred over a magnetic stirrer at 1500 rpm for 10 minutes. Acetone (25 ml) was added to the stirring solution, and the mixture was left stirring for 10 minutes. The mixture was heated at 70° C. for 30 minutes with stirring at 5000 rpm to stabilize the protein particles. The protein particles were then sized in a Malvern Master sizer for future use (the protein particles were about 250 nm).

EXAMPLE 2

Preparation of Large Ovalbumin (OVA) Protein Particles

Ovalbumin (OVA, 200 mg) was dissolved in distilled water (10 ml) to form a 2% protein solution. Lactic acid (100 μl) was added to the OVA-solution until the pH was reduced to about 4.5–5.0. The solution was stirred over a magnetic stirrer at 500 rpm for 10 minutes. Acetone (25 ml) was added to the stirring solution, and the mixture was left stirring for 10 minutes. The mixture was heated at 70° C. and stirred at 500 rpm for 30 minutes to stabilize the protein particles. The protein particles were lyophilized and then sized in a Malvern Master sizer and stored in a dessicator for future use (the protein particles were about 2.5 μm).

EXAMPLE 3

Preparation of Small gB2 Protein Particles

HSVgB2 antigen (4.2 mg) was dissolved in distilled water (2 ml), and the solution was stirred over a magnetic stirrer at 1500 rpm. Acetone (2.5 ml) was added to the stirring solution, and the mixture was left stirring for 20 minutes. The mixture was then heated at 70° C. and left stirring for 25 minutes to stabilize the protein particles. The mixture was centrifuged at 30,000× g and the protein particles were collected. The particles were lyophilized and then sized in a Malvern Master sizer for future use (the protein particles were about 350 nm).

EXAMPLE 4

Preparation of Large gB2 Protein Particles

HSVgB2 antigen (4.2 mg) was dissolved in distilled water (2 ml), and the solution was stirred over a magnetic stirrer at 750 rpm. Acetone (2.5 ml) was added to the stirring solution, and the mixture was left stirring for 20 minutes. The mixture was then heated at 70° C. and left stirring for 25 minutes to stabilize the protein particles. The mixture was centrifuged at 30,000× g and the protein particles were collected. The protein particles were lyophilized and then sized in a Malvern Master sizer for future use (the protein particles were about 5 μm).

EXAMPLE 5

Preparation of PLG Particles

PLG (poly(lactideco-glycolides)) particles were made using polyvinyl alcohol (PVA) as follows. Solutions used:
(1) 66% RG 503 PLG (Boehringer Ingelheim) in dichloromethane.
(2) 8% polyvinyl alcohol (PVA) (ICN) in water.

In particular, the PLG particles were made by combining 10 ml of polymer solution with 40 ml of the PVA solution and homogenizing for 3 minutes using an Omni benchtop homogenizer with a 10 mm probe at 10K rpm. The emulsion was left stirring overnight for solvent evaporation. The formed PLG particles were washed with water by centrifugation 4 times, and lyophilized. The PLG particles were then sized in a Malvern Master sizer for future use.

EXAMPLE 6

Preparation of PLG OVA-Entrapped Particle Using A Solvent Evaporation Technique

In a 15 ml glass test tube was placed 1 ml of 10 mg/m OVA and 20 ml of 5% w:w PLG (poly D,L-lactide-co-glycolide) in dichloromethane, 50:50 mol ratio lactide to glycolide, MW average=70–100 kDa, (Medisorb Technologies International). The solution was homogenized for 2 minutes at high rpm using a hand held homogenizer. The homogenate was added to 80 ml of 10% polyvinyl alcohol (PVA) (12–23 kDa) in a 100 ml glass beaker. This was homogenized for two minutes at a 10,000 rpm using a bench scale homogenizer equipped with a 20 mm diameter generator. The solution was stirred at room temperature at a moderate rate using a magnetic stir bar until the solvents were evaporated. PLG OVA-entrapped particles were resuspended in water and washed several times with water, using centrifugation to pellet the particles between washes. The particles were dried in the presence of desiccant (Dririte $CaSO_4$) under vacuum. Mean volume size was determined to be 0.9 μm by laser diffraction measurement. Protein content of the PLG OVA-entrapped particles was determined to be 0.8% w:w by amino acid compositional analysis.

EXAMPLE 7

Immunogenicity of Ovalbumin (OVA) Particles

Ovalbumin, PLG/OVA-entrapped particles, small OVA-protein particles (250 nm) and large OVA-protein particles (2500 nm), produced as described above, were administered subcutaneously to mice (dose=10 μg). The animals were boosted at 1M and 28 days. Serum was collected two weeks following the last immunizadon and CTL activity assayed as described in Doe et al., *Proc. Natl. Acad. Sci.* (1996) 93:8578–8583.

The lymphocyte cultures were prepared as follows. Spleen cells (sc) from immunized mice were cultured in 24-well dishes at $5\times10^6$ cells per well. Of those cells, $1\times10^6$ were sensitized with synthetic epitopic peptides from EG7 (EL4 transfected with ovalbumin) and EL4 proteins at a concentration of 10 μM for 1 hour at 37° C., washed, and cocultured with the remaining $4\times10^6$ untreated sc in 2 ml of culture medium [50% RPMI 1640 and 50% alpha-MEM (GIBCO)] supplemented with heat-inactivated fetal if serum, $5\times10^{-5}$ M 2-mercaptoethanol, antibiotics, and 5% interleukin 2 (Rat T-Stim, Collaborative Biomedical Products, Bedford, Mass.). Cells were fed with 1 ml of fresh culture medium on days 3 and 5, and cytotoxicity was assayed on day 6.

The cytotoxic cell assay was conducted as follows. EG7 (EL4 transfected with ovalbumin) and EL4 target cells used in the $^{51}$Cr release assays express class I but not class II MHC molecules. Approximately 1×10$^6$ target cells were incubated in 200 μl of medium containing 50 μCi (1 Ci=37 Gbq) of $^{51}$Cr and synthetic Ovalbumin peptides (1 μm) for 60 min and washed three times. Effector (E) cells were cultured with 5×10$^3$ target (T) cells at various EST ratios in 200 μl of culture medium in 96-well round-bottom tissue culture plates for 4 hours. The average cpm from duplicate wells was used to calculate percent specific $^{51}$Cr release.

As shown in FIG. 1, the small and large OVA-protein particles elicited a CTL response and the small OVA-protein particles had activity comparable to the large OVA-protein particles. Both types of OVA-protein particles were more active than the PLG/OVA-entrapped particles and ovalbumin alone formulations.

EXAMPLE 8

Preparation of PLG gB2-Entrapped Particle Using A Solvent Evaporation Technique

In a 15 ml glass test tube was placed 0.5 ml 5 mg/ml gB2 and 5 ml 6% w:w PLG (poly D,L-lactide-co-glycolide) in dichloromethane, 50:50 mol ratio lactide to glycolide, MW average=70–100 kDa, (Medisorb Technologies International). The solution was homogenized for 2 minutes at high rpm using a hand held homogenizer. The homogenate was added to 20 ml 8% polyvinyl alcohol (PVA) (12–23 kDa) in a 100 ml glass beaker. The mixture was homogenized for two minutes at a 10,000 rpm using a bench scale homogenizer equipped with a 20 mm diameter generator, The solution was stirred at room temperature at a moderate rate using a magnetic stir bar until the solvents were evaporated. PLG gB2-entrapped particles were resuspended in water and washed several times with water, using centrifugation to pellet the particles between washes. The particles were dried in the presence of desiccant (Dririte CasO$_4$) under vacuum. Mean volume size was determined to be 0.9 μm by laser diffraction measurement. Protein content of the PLG gB2-entrapped particles was determined to be 0.5% w:w by amino acid compositional analysis.

EXAMPLE 9

Immunogenicity of gB2 Particles

The gB2 protein particles, PLG gB2-entrapped particles, produced as described above, as well as gB2 alone, without associated protein particles (as a negative control) and vaccinia gag-pol controls (as a positive control) were administered subcutaneously to mice (dose=5 μg). The animals were boosted at 7 and 14 days. Serum was collected two weeks following the last immunization and CTL activity assayed as described in Doe et al., Proc. Natl. Acad. Sci. (19%) 93:8578–8583.

The lymphocyte cultures were prepared as follows. Spleen cells (sc) from immunized mice were cultured in 24-well dishes at 5×10$^6$ cells per well. Of those cells, 1×10$^6$ were sensitized with synthetic epitopic peptides from HIV-1$_{SF2}$ proteins at a concentration of 10 μM for 1 hour at 37° C., washed, and cocultured with the remaining 4×10$^6$ untreated sc in 2 ml of culture medium [50% RPMI 1640 and 50% alpha-MEM (GIBCO)] supplemented with heat-inactivated fetal calf serum, 5×10$^{-5}$ M 2-mercaptoethanol, antibiotics, and 5% interleukin 2 (Rat T-Stim, Collaborative Biomedical Products, Bedford, Mass.). Cells were fed with 1 ml of fresh culture medium on days 3 and 5, and cytotoxicity was assayed on day 6.

The cytotoxic cell assay was conducted as follows. SvBALB (H-2$^d$) (SvB) and MCS7 (H-2$^b$) target cells used in the $^{51}$Cr release assays express class I but not class II MHC molecules. Approximately 1×10$^6$ target cells were incubated in 200 μl of medium containing 50 μCi (1 Ci=37 Gbq) of $^{51}$Cr and synthetic HIV-1 peptides (1 mM) for 60 min and washed three times. Effector (E) cells were cultured with 5×10$^3$ target (T) cells at various E/T ratios in 200 μl of culture medium in 96-well round-bottom tissue culture plates for 4 hours. The average cpm from duplicate wells was used to calculate percent specific $^{51}$Cr release.

Figure 2:
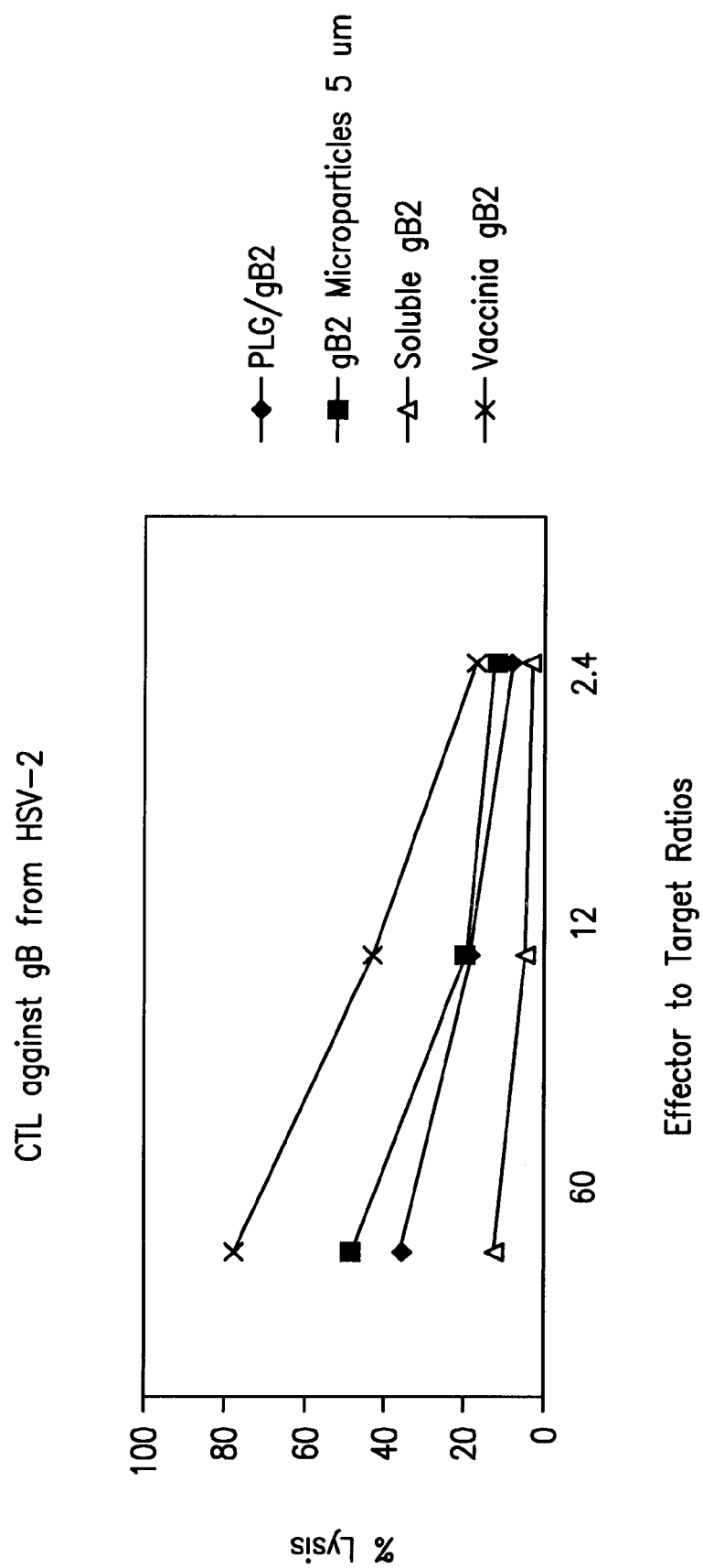
FIG. 2 illustrates the CTL activity of gB2 protein formulation, gB2 protein particles and the PLG/gB2-entrapped particles.

As shown in FIG. 2, the gB2 protein particles were less active than the vaccinia control and were more active than the PLG/gBf2-entrapped particles and the gB2 protein formulation.

Thus, novel protein particle antigen compositions and methods for using and making the same are disclosed. Although preferred embodiments of the subject invention have been described in some detail, it is understood that obvious variations can be made without departing from the spirit and the scope of the invention as defined by the appended claims.

We claim:

1. A stabilized protein particle produced by a process comprising:
    (a) providing an aqueous solution comprising a protein antigen;
    (b) combining a precipitation agent with the aqueous solution;
    (c) dispersing the resultant mixture to form protein particles;
    (d) stabilizing said protein particles by a stabilizing treatment; and
    (e) recovering said stabilized protein particle;
wherein said stabilized protein particle is not a virus-like particle, and wherein said stabilized protein particle is not entrapped within a carrier particle.

2. An immunogenic composition comprising the stabilized protein particle of claim 1 and a pharmaceutically acceptable excipient.

3. The stabilized protein particle of claim 1, wherein said aqueous solution contains between 5% and 90% water.

4. The stabilized protein particle of claim 1, wherein said resultant mixture is dispersed by stirring.

5. The immunogenic composition of claim 2 wherein said immunogenic composition is capable of producing a cellular immune response.

6. The immunogenic composition of claim 5 wherein the cellular immune response is a cytotoxic-T lymphocyte response.

7. The immunogenic composition of claim 2 wherein the protein particle is formed from a protein antigen selected from the group consisting of a viral, a fungal, a bacterial, an avian and a mammalian protein.

8. The immunogenic composition of claim 7 wherein the protein antigen is herpes simplex virus type 2 glycoprotein B (HSV gB2), hepatitis C virus (HCV) or a human immunodeficiency virus (HIV) protein.

9. The immunogenic composition of claim 8, wherein the HCV protein is HCV core protein, E1, E2, NS3, NS4, or NS5.

10. The immunogenic composition of claim 8, wherein the HIV protein is gp120, gp160, gp41, p24gag or p55gag.

11. The immunogenic composition of claim 2 wherein the aqueous solution in step (a) further comprises an acid.

12. The immunogenic composition of claim 11 wherein the acid is acetic acid, glycolic acid, hydroxybutyric acid, hydrochloric acid or lactic acid.

13. The immunogenic composition of claim 2 wherein the precipitation agent comprises an oil, a hydrocarbon or a coacervation agent.

14. The immunogenic composition of claim 2 wherein the stabilizing treatment comprises heat treatment or treatment with a chemical cross-linking agent.

15. The immunogenic composition of claim 14 wherein the stabilizing treatment is heat treatment.

16. The immunogenic composition of claim 2, further comprising an adjuvant.

17. The immunogenic composition of claim 16, wherein said adjuvant comprises squalene or a detoxified mutant of an E. coli heat-labile toxin.

18. The immunogenic composition of claim 2 further comprising an additional antigen, wherein said additional antigen is distinct from said protein particle.

19. The immunogenic composition of claim 18 wherein said additional antigen is adsorbed on to, or encapsulated within a carrier, wherein said carrier is selected from the group consisting of proteins, polysaccharides, polylactic acids, polyglycollic acids, polymeric amino acids, amino acid copolymers, lipid aggregates, polymeric particles and inactive virus particles.

20. The immunogenic composition of claim 19 wherein said polymeric particle comprises a polymer selected from the group consisting of a poly($\alpha$-hydroxy acid), a polyhydroxy butyric acid, a polycaprolactone, a polyorthoester, and a polyanhydride.

21. The immunogenic composition of claim 2, further comprising an additional antigen wherein said additional antigen is conjugated on to said protein particle.

22. The immunogenic composition of claim 2, wherein said stabilized protein particle is generally spherical.

23. The immunogenic composition of claim 22, wherein said stabilized protein particle has a diameter ranging from 200 nanometers to 10 microns.

24. The immunogenic composition of claim 22, wherein said stabilized protein particle has a diameter ranging from 500 nanometers to 5 microns.

25. The immunogenic composition of claim 7, wherein said protein antigen is a tumor protein.

26. The immunogenic composition of claim 7, wherein said protein antigen is a viral protein selected from the group consisting of HIV, herpes simplex virus, hepatitis virus, and influenza A virus proteins.

27. The immunogenic composition of claim 7, wherein said protein antigen is a bacterial protein selected from the group consisting of pertussis, diphtheria, meningitis, H. pylori, Ilemophilus influenza B, and tetanus proteins.

28. The immunogenic composition of claim 2, wherein said immunogenic composition is an injectable vaccine composition.

29. A method of making the immunogenic composition of claim 2, comprising:

(a) providing an aqueous solution comprising a protein antigen;

(b) combining a precipitation agent with the aqueous solution;

(c) dispersing the resultant mixture to form protein particles;

(d) stabilizing said dispersed protein particles by a stabilizing treatment;

(e) recovering said stabilized protein particle; and (f) combining the stabilized protein particle with a pharmaceutically acceptable excipient.

30. A method for raising an immune response in a vertebrate subject comprising administering to said vertebrate subject an amount of the immunogenic composition of claim 2 effective to raise an immune response.

31. The method of claim 30, wherein said immune response is a cytotoxic-T lymphocyte (CTL) response.

32. The method of claim 30, wherein said immunogenic composition is administered by injection.

33. The method of claim 30, wherein said immune response is an antibody-mediated immune response.

34. The method of claim 2, wherein said protein antigen in said stabilized protein particle is cross-linked.

35. A stabilized protein particle capable of producing a cytotoxic-T lymphocyte (CTL) response, wherein said stabilized protein particle is a generally spherical particle that is produced by a process comprising: (a) forming a protein particle from protein antigen and (b) stabilizing the protein particle by a stabilizing treatment, wherein said stabilized protein particle is not a virus-like particle, and wherein said stabilized protein particle is not entrapped within a carrier.

36. A method of preparing an immunogenic composition comprising providing the stabilized protein particle of claim 35, and combining said stabilized protein particle with a pharmaceutically acceptable excipient.

37. The method of claim 36, further comprising providing an additional antigen within said immunogenic composition, wherein said additional antigen is distinct from said protein particle.

38. The method of claim 36, wherein said stabilized protein particle has a diameter ranging from 200 nanometers to 10 microns.

39. The method of claim 36, wherein said stabilized protein particle has a diameter ranging from 500 nanometers to 5 microns.

40. The method of claim 36, wherein said stabilizing treatment is a heat treatment process.

41. The method of claim 36, wherein said stabilizing treatment is a chemical cross-linking process.

42. The method of claim 36, wherein said protein particle is formed by a precipitation process.

43. The method of claim 36, wherein said precipitation process comprises combining an aqueous protein solution with an oil, a hydrocarbon or a coacervation agent.

44. The method of claim 36, wherein said protein particle is formed by an emulsion process.

45. The method of claim 36, wherein said stabilized protein particle is formed using a tumor protein antigen.

46. The method of claim 36, wherein said stabilized protein particle is formed using a viral protein antigen.

47. The method of claim 36, wherein said stabilized protein particle is formed using a bacterial protein antigen.

48. An immunogenic composition formed by the method of claim 36.

49. The method of claim 36, wherein said protein antigen in said stabilized protein particle is cross-linked.

* * * * *